(12) United States Patent
Lee et al.

(10) Patent No.: US 9,200,298 B2
(45) Date of Patent: Dec. 1, 2015

(54) HOST CELLS AND METHODS FOR PRODUCING ISOPRENYL ALKANOATES

(75) Inventors: Taek Soon Lee, Albany, CA (US); Jeffrey L. Fortman, San Francisco, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 203 days.

(21) Appl. No.: 12/644,531

(22) Filed: Dec. 22, 2009

(65) Prior Publication Data

US 2010/0180491 A1 Jul. 22, 2010

Related U.S. Application Data

(63) Continuation of application No. PCT/US2008/068756, filed on Jun. 30, 2008.

(60) Provisional application No. 60/947,280, filed on Jun. 29, 2007.

(51) Int. Cl.
| | |
|---|---|
| *C12P 7/62* | (2006.01) |
| *C12N 1/12* | (2006.01) |
| *C12N 1/20* | (2006.01) |
| *C12N 5/00* | (2006.01) |
| *C12N 1/18* | (2006.01) |

(52) U.S. Cl.
CPC ... *C12P 7/62* (2013.01); *C12N 1/18* (2013.01); *C12N 1/20* (2013.01)

(58) Field of Classification Search
CPC ............... C12N 1/18; C12N 1/20; C12P 7/62
USPC .................... 44/401; 435/135, 252.3, 252.31, 435/252.33, 252.34, 325, 348, 354.2, 254.1, 435/254.11, 254.2
See application file for complete search history.

(56) References Cited

U.S. PATENT DOCUMENTS

| | | | |
|---|---|---|---|
| 4,683,195 | A | 7/1987 | Mullis et al. |
| 5,460,949 | A | 10/1995 | Saunders et al. |
| 5,521,088 | A | 5/1996 | Fujii et al. |
| 5,728,412 | A | 3/1998 | Fujii et al. |
| 5,853,433 | A | 12/1998 | Spencer et al. |
| 6,190,895 | B1 | 2/2001 | Croteau et al. |
| 6,291,745 | B1 | 9/2001 | Meyer et al. |
| 6,353,143 | B1 | 3/2002 | Fang et al. |
| 6,531,303 | B1 | 3/2003 | Millis et al. |
| 6,689,593 | B2 | 2/2004 | Millis et al. |

(Continued)

OTHER PUBLICATIONS

Armstrong et al. Natural flavors produced by biotechnological processing, American Chemical Society, Washington, DC, 1989.

(Continued)

*Primary Examiner* — James Goloboy
*Assistant Examiner* — Latosha Hines
(74) *Attorney, Agent, or Firm* — Robin C. Chiang; Lawrence Berkeley National Laboratory

(57) ABSTRACT

The invention provides for a method of producing an isoprenyl alkanoate in a genetically modified host cell. In one embodiment, the method comprises culturing a genetically modified host cell which expresses an enzyme capable of catalyzing the esterification of an isoprenol and a straight-chain fatty acid, such as an alcohol acetyltransferase (AAT), wax ester synthase/diacylglycerol acyltransferase (WS/DGAT) or lipase, under a suitable condition so that the isoprenyl alkanoate is produced.

27 Claims, 4 Drawing Sheets

(56) References Cited

U.S. PATENT DOCUMENTS

| | | | |
|---|---|---|---|
| 7,118,896 B2 | 10/2006 | Kalscheuer et al. | |
| 7,172,886 B2 | 2/2007 | Keasling et al. | |
| 7,183,089 B2 | 2/2007 | Keasling et al. | |
| 7,192,751 B2 | 3/2007 | Keasling et al. | |
| 7,390,643 B2 * | 6/2008 | Croteau et al. | 435/196 |
| 2003/0148479 A1 | 8/2003 | Keasling et al. | |
| 2004/0005678 A1 | 1/2004 | Keasling et al. | |
| 2004/0009576 A1 | 1/2004 | Kalscheuer et al. | |
| 2004/0029239 A1 | 2/2004 | Ohto et al. | |
| 2004/0063182 A1 | 4/2004 | Ohto et al. | |
| 2004/0072323 A1 | 4/2004 | Matsuda et al. | |
| 2004/0077039 A1 | 4/2004 | Holtzman | |
| 2004/0101865 A1 * | 5/2004 | Cirpus et al. | 435/6 |
| 2004/0110259 A1 | 6/2004 | Baugh et al. | |
| 2004/0194162 A1 | 9/2004 | Hahn et al. | |
| 2005/0204417 A1 | 9/2005 | Croteau et al. | |
| 2006/0079476 A1 | 4/2006 | Keasling et al. | |
| 2007/0015237 A1 * | 1/2007 | Bailey et al. | 435/67 |
| 2007/0077616 A1 | 4/2007 | Keasling et al. | |
| 2007/0092931 A1 | 4/2007 | Keasling et al. | |
| 2007/0099261 A1 | 5/2007 | Keasling et al. | |

OTHER PUBLICATIONS

Brock and Buckel. On the mechanism of action of the antifungal agent propionate. Eur. J. Biochem. 271: 3227-3241, 2004.
Choi and Lee. High-level production of poly(3-hydroxybutyrate-co-3-hydroxyvalerate) by fed-batch culture of recombinant *Escherichia coli*. Appl. Environ. Microbiol. 65: 4363-4368, 1999.
deBoer et al. The tac promoter: a functional hybrid derived from the trp and lac promoters. Proc. Natl. Acad. Sci. Usa, 80:21-25, 1983.
Dehesh et al., Two novel thioesterases are key determinants of the bimodal distribution of acyl chain length of Cuphea palustris seed oil. Plant Physiol. 110:203-10, 1996.
Donald et al. Effects of overproduction of the catalytic domain of 3-hydroxy-3-methylglutaryl coenzyme a reductase on squalene synthesis in *Saccharomyces cerevisiae*. Appl. Env. Microbiol. 63:3341-3344, 1997.
Farrell et al., Ethanol can contribute to energy and environmental goals. Science. 311:506, 2006.
Floss and Yu. Lessons from the rifamycin biosynthetic gene cluster. Curr. Opin. Chem. Biol. 3:592, 1999.
Fujii et al., Molecular cloning, sequence analysis, and expression of the yeast alcohol acetyltransferase gene. Appl. Environ. Microbiol. 60(8):2786-2792, 1994.
Fujii et al., Nucleotide sequences of alcohol acetyltransferase genes from lager brewing yeast, *Saccharomyces carlsbergensis*. Yeast 12(6): 593-598, 1996.
Gray et al., Bioethanol. Curr Opin Chem Biol. 10:141, 2006.
Hamano et al. Cloning of a gene cluster encoding enzymes responsible for the mevalonate pathway from a terpenoidantibiotic-producing Streptomyces strain. Biosci. Biotechnol. Biochem. 65:1627-1635, 2001.
Hitchman et al., Hexanoate Synthase, a Specialized Type I Fatty Acid Synthase in Aflatoxin B1 Biosynthesis. Bioorg Chem. 29:293-307, 2001.
Horton et al. Heterologous expression of the *Saccharomyces cerevisiae* alcohol acetyltransferase genes in Clostridium acetobutylicum and *Escherichia coli* for the production of isoamyl acetate. J. Ind. Microbiol. Biotechnol. 30:427-432, 2003.
Ijima et al. Characterization of geraniol synthase from the peltate glands of sweet basil. Plant Physiology. 134:370-379, 2004.
Jackson et al. Metabolic engineering to produce sesquiterpenes in yeast. Organ. Lett. 5:1629-1632, 2003.
Kalscheuer et al. Synthesis of novel lipids in *Saccharomyces cerevisiae* by heterologous expression of an unspecific bacterial acyltransferase. Appl. Environ. Microbiol. 70:7119-7125, 2004.
Kalscheuer et al., in vitro and in vivo biosynthesis of wax diesters by an unspecific bifunctional wax ester synthase! acyl-CoA:diacylglycerol acyltransferase from Acinetobacter calcoaceticus ADP1. Eur. J. Lipid Sci. Technol. 105:578-584, 2003.

Kalscheuer et al. A Novel Bifunctional Wax Ester Synthase/Acyl-CoA:Diacylglycerol Acyltransferase Mediates Wax Ester and Triacylglycerol Biosynthesis in Acinetobacter calcoaceticus ADP1. J. Biol. Chem. 278: 8075-8082, 2003.
Kalscheuer et al. Microdiesel: *Escherichia coli* engineered for fuel production. Microbiol. 152, 2529-2536, 2006.
Kuzuyama et al. Heterologous mevalonate production in Streptomyces lividans TK23. Biosci. Biotechnol. Biochem. 68 (4): 931-934, 2004.
Lee et al., Fatty acid synthesis by elongases in trypanosomes. Cell. 126:691, 2006.
Martin et al., Engineering a mevalonate pathway in *Escherichia coli* for production of terpenoids. Nat. Biotech. 21 (7):796-802, 2003.
Murli et al. Metabolic engineering of *Escherichia coli* for improved 6-deoxyerythronolide B production. J. Ind. Microbiol. Biotechnol. 30: 560-509, 2003.
Naggert et al., Expression in *Escherichia coli*, purification and characterization of two mammalian thioesterases involved in fatty acid synthesis. Biochem. J. 273 (Pt 3): 787, 1991.
Parke et al., Toxicity caused by hydroxycinnamoyl-coenzyme a thioester accumulation in mutants of Acinetobacter sp. strain ADP1. Appl. Environ. Microbiol. 70: 2974-2983, 2004.
Pimentel and Patzek, Ethanol Production Using Corn, Switchgrass, and Wood; Biodiesel Production Using Soybean and Sunflower. Natural Resources Research. 14:65, 2005.
Polakowski et al. Overexpression of a cytosolic hydroxymethylglutaryl-CoA reductase leads to squalene accumulation in yeast. Appl. Microbiol. Biotechnol. 49: 67-71, 1998.
Pollard et al., A specific acyl-Acp thioesterase implicated in medium-chain fatty acid production in immature cotyledons of Umbellularia californica. Arch Biochem Biophys. 284:306, 1991.
Ramos et al., Mechanisms of solvent tolerance in gram-negative bacteria. Annu Rev Microbiol. 56:743, 2002.
Reiling et al., Mono and diterpene production in *Escherichia coli*. Biotechnol. Bioeng. 87(2):200-212, 2004.
Ro et al., Production of the antimalarial drug precursor artemisinic acid in engineered yeast. Nature. 440:940-3, 2006.
Smith et al., New insights into Acinetobacter baumannii pathogenesis revealed by high-density pyrosequencing and transposon mutagenesis. Genes Dev. 21:601-614, 2007.
Song, A soluble form of phosphatase in *Saccharomyces cerevisiae* capable of converting farnesyl diphosphate into E, E-farnesol. Appl. Biochem. Biotechnol. 128:149-58, 2006.
Steveken et al., The wax ester synthase/acyl coenzyme A:diacylglycerol acyltransferase from Acinetobacter sp. strain ADP1: characterization of a novel type of acyltransferase. J. Bacteriol. 187:1369-1376, 2005.
Subrahmanyam et al., Overproduction of a functional fatty acid biosynthetic enzyme blocks fatty acid synthesis in *Escherichia coli*. J. Bacteriol. 180: 4596-4602, 1998.
Tabata and Hashimoto. Production of mevalonate by a metabolically-engineered *Escherichia coli*. Biotechnol. Lett. 26:1487-1491, 2004.
Uthoff et al. Thio wax ester biosynthesis utilizing the unspecific bifunctional wax ester synthase/acyl coenzyme A: diacylglycerol acyltransferase of Acinetobacter sp. strain ADP1. Appl. Environ. Microbiol. 71:932-936, 2005.
Vaneechoutte et al. Naturally transformable Acinetobacter sp. strain ADP1 belongs to the newly described species Acinetobacter baylyi. Appl. Environ. Microbiol. 72:932-936, 2006.
Verstrepen et al., Expression levels of the yeast alcohol acetyltransferase genes ATF1, Lg-ATF1, and ATF2 control the formation of a broad range of volatile esters. Appl. Environ. Microbiol. 69(9): 5228-5237, 2003.
White et al., The structural biology of type II fatty acid biosynthesis. Ann. Rev. Biochem. 74:791-831, 2005.
Wilding et al., Identification, evolution, and essentiality of the mevalonate pathway for isopentenyl diphosphate biosynthesis in gram-positive cocci. J. Bacteriol. 182(15): 4319-27, 2000.
IPRP, Int'l Appl. PCT/US2008/068756 (mailed May 25, 2010).
ISR/WO, Int'l Appl. PCT/US2008/068756 (mailed Sep. 29, 2009).

* cited by examiner

A

| No | Prediction | Result | No | Prediction | Result |
|---|---|---|---|---|---|
| 1 | 14.6 | 11.2 | 19 | 46.4 | |
| 2 | 32.3 | | 20 | 47.0 | 42.2 |
| 3 | 32.3 | 23.9 | 21 | 39.7 | |
| 4 | 28.6 | 15.6 | 22 | 56.7 | |
| 5 | 49.6 | | 23 | 56.7 | 64.4 |
| 6 | 61.0 | | 24 | 67.0 | |
| 7 | 17.8 | | 25 | 55.8 | |
| 8 | 30.7 | 25.3 | 26 | 53.5 | |
| 9 | 25.5 | 32.5 | 27 | 43.0 | |
| 10 | 31.9 | | 28 | 65.2 | |
| 11 | 47.8 | 38 | 29 | 74.4 | |
| 12 | 55.2 | | 30 | 73.2 | |
| 13 | 34.1 | | 31 | 9.1 | 12.2 |
| 14 | 37.7 | 43.4 | 32 | 15.6 | 13.2 |
| 15 | 31.3 | 34.3 | 33 | 23.0 | 17.3 |
| 16 | 45.1 | | 34 | 25.7 | 28.8 |
| 17 | 57.8 | 50.7 | 35 | 37.7 | 21 |
| 18 | 61.2 | | 36 | 44.8 | |

SEQUENCE LISTING

<160> NUMBER OF SEQ ID NOS: 11

<210> SEQ ID NO 1
<211> LENGTH: 77
<212> TYPE: PRT
<213> ORGANISM: Mycobacterium tuberculosis

<400> SEQUENCE: 1

```
Leu Gly Tyr His Ala Arg Arg Ser Ala Leu Pro Ala Pro Gly Arg Val
1               5                   10                  15

Arg Glu Leu Leu Glu Leu Thr Ser Arg Leu His Ser Asn Leu Leu Asp
            20                  25                  30

Arg His Arg Pro Leu Trp Glu Thr His Val Ile Glu Gly Leu Arg Asp
        35                  40                  45

Gly Arg Phe Ala Ile Tyr Ser Lys Met His His Ala Leu Val Asp Gly
```

```
                    50                  55                  60
Val Ser Gly Leu Thr Leu Met Arg Gln Pro Met Thr Thr
 65                  70                  75

<210> SEQ ID NO 2
<211> LENGTH: 77
<212> TYPE: PRT
<213> ORGANISM: Mycobacterium tuberculosis

<400> SEQUENCE: 2

Leu Asp Tyr His Val Arg Arg Ser Ala Leu Pro Ser Pro Gly Arg Val
  1               5                  10                  15

Arg Asp Leu Leu Glu Leu Thr Ser Arg Leu His Thr Ser Leu Leu Asp
                 20                  25                  30

Arg His Arg Pro Leu Trp Glu Leu His Val Val Glu Gly Leu Asn Asp
             35                  40                  45

Gly Arg Phe Ala Met Tyr Thr Lys Met His His Ala Leu Ile Asp Gly
         50                  55                  60

Val Ser Ala Met Lys Leu Ala Gln Arg Thr Leu Ser Ala
 65                  70                  75

<210> SEQ ID NO 3
<211> LENGTH: 77
<212> TYPE: PRT
<213> ORGANISM: Mycobacterium tuberculosis

<400> SEQUENCE: 3

Leu Asp Phe His Ile Arg Arg Ile Gly Val Pro Ala Pro Gly Gly Arg
  1               5                  10                  15

Arg Glu Leu Glu Glu Leu Val Gly Arg Leu Met Ser Tyr Lys Leu Asp
                 20                  25                  30

Arg Ser Arg Pro Leu Trp Glu Leu Trp Val Ile Glu Gly Val Glu Gly
             35                  40                  45

Gly Arg Ile Ala Thr Leu Thr Lys Met His His Ala Ile Val Asp Gly
         50                  55                  60

Val Ser Gly Ala Gly Leu Gly Glu Ile Leu Leu Asp Ile
 65                  70                  75

<210> SEQ ID NO 4
<211> LENGTH: 77
<212> TYPE: PRT
<213> ORGANISM: Mycobacterium tuberculosis

<400> SEQUENCE: 4

Leu Asp Tyr His Val Arg Arg Ser Ala Leu Ala Ser Pro Gly Asp Glu
  1               5                  10                  15

Arg Glu Leu Gly Ile Pro Val Ser Arg Leu His Ser His Ala Leu Asp
                 20                  25                  30

Leu Arg Arg Pro Pro Trp Glu Val His Phe Ile Glu Gly Leu Glu Gly
             35                  40                  45

Gly Arg Phe Ala Ile Tyr Ile Lys Met His His Ser Leu Ile Asp Gly
         50                  55                  60

Tyr Thr Gly Gln Lys Met Leu Ala Arg Ser Leu Ser Thr
 65                  70                  75

<210> SEQ ID NO 5
<211> LENGTH: 77
<212> TYPE: PRT
<213> ORGANISM: Mycobacterium tuberculosis
```

<400> SEQUENCE: 5

Pro Ser Tyr His Val Arg Leu Ser Ala Leu Pro Tyr Pro Gly Thr Gly
1               5                   10                  15

Arg Asp Leu Gly Ala Leu Val Glu Arg Leu His Ser Thr Pro Leu Asp
            20                  25                  30

Met Ala Lys Pro Leu Trp Glu Leu His Leu Ile Glu Gly Leu Thr Gly
        35                  40                  45

Arg Gln Phe Ala Met Tyr Phe Lys Ala His His Cys Ala Val Asp Gly
    50                  55                  60

Leu Gly Gly Val Asn Leu Ile Lys Ser Trp Leu Thr Thr
65                  70                  75

<210> SEQ ID NO 6
<211> LENGTH: 82
<212> TYPE: PRT
<213> ORGANISM: Arabidopsis thaliana

<400> SEQUENCE: 6

Val Glu Asp His Val Phe Val Pro Asp Ile Asp Leu Gln Glu Ile Asn
1               5                   10                  15

Lys Asp Gly Asp Gly Phe Val Asp Asp Tyr Val Ser Arg Leu Thr Leu
            20                  25                  30

Ser Pro Leu Asp Lys Ser Lys Pro Leu Trp Asp Ile His Ile Leu Asn
        35                  40                  45

Val Lys Thr Ser Asp Ala Glu Ala Val Gly Val Met Arg Cys His His
    50                  55                  60

Ser Leu Ala Asp Gly Met Ser Leu Met Ser Leu Leu Val Ala Cys Thr
65                  70                  75                  80

Arg Lys

<210> SEQ ID NO 7
<211> LENGTH: 82
<212> TYPE: PRT
<213> ORGANISM: Arabidopsis thaliana

<400> SEQUENCE: 7

Val Glu Asp His Val Ile Val Pro Tyr Ile Asp Pro Glu Asp Ile Cys
1               5                   10                  15

Glu Gly Gly Gln Ser Phe Val Asp Asp Tyr Ile Ser Arg Leu Thr Leu
            20                  25                  30

Ile Pro Leu Asp Arg Ser Arg Pro Leu Trp Asp Ile His Ile Leu Asn
        35                  40                  45

Val Lys Thr Ser Tyr Ala Glu Ala Val Gly Val Ile Arg Phe Asn His
    50                  55                  60

Ala Leu Ala Asp Gly Met Ser Phe Ile Ser Leu Val Leu Ala Cys Thr
65                  70                  75                  80

His Lys

<210> SEQ ID NO 8
<211> LENGTH: 83
<212> TYPE: PRT
<213> ORGANISM: Arabidopsis thaliana

<400> SEQUENCE: 8

Val Glu Asp His Val Ile Val Pro Tyr Ile Asp Ala Glu Glu Ile Gly
1               5                   10                  15

```
Glu Gly Gly Gln Ser Phe Ile Asp Asp Tyr Met Ser Arg Leu Thr Met
                20                  25                  30

Ile Pro Leu Asp Arg Ser Arg Pro Leu Trp Asp Ile His Ile Leu Asn
            35                  40                  45

Val Lys Lys Thr Ser Glu Ala Glu Ala Val Gly Phe Ile Arg Ser His
    50                  55                  60

His Ser Leu Ala Asp Gly Met Ser Phe Ile Ser Leu Met Leu Ala Cys
65                  70                  75                  80

Thr His Lys

<210> SEQ ID NO 9
<211> LENGTH: 82
<212> TYPE: PRT
<213> ORGANISM: Arabidopsis thaliana

<400> SEQUENCE: 9

Val Glu Glu His Val Phe Val Pro Asp Ile Asp Pro Lys Leu Thr Glu
1               5                   10                  15

Glu Asp Val Glu Trp Phe Val Glu Asp Tyr Ile Ser Ser Ile Thr Met
                20                  25                  30

Ile Pro Leu Asp Arg Thr Lys Pro Leu Trp Glu Val His Ile Leu Asn
            35                  40                  45

Ala Lys Thr Ser Asp Ala Glu Ala Ile Cys Val Ile Arg Cys His His
    50                  55                  60

Ala Leu Gly Asp Gly Val Ser Ile Leu Ser Leu Ile Leu Ala Ser Thr
65                  70                  75                  80

Arg Lys

<210> SEQ ID NO 10
<211> LENGTH: 80
<212> TYPE: PRT
<213> ORGANISM: Arabidopsis thaliana

<400> SEQUENCE: 10

Val Glu Glu His Val Ile Val Pro Asp Ile Asp Pro Asn Ile Glu Asn
1               5                   10                  15

Pro Asp Glu Phe Leu Glu Asp Tyr Thr Ser Asn Met Ala Leu Ser Pro
                20                  25                  30

Met Asp Met Ser Lys Pro Leu Trp Glu Phe His Leu Leu Lys Leu Lys
            35                  40                  45

Thr Ser His Ala Glu Ala Val Thr Val Ala Arg Phe His His Ser Leu
    50                  55                  60

Gly Asp Gly Met Ser Leu Met Ser Leu Leu Leu Ala Cys Thr Arg Lys
65                  70                  75                  80

<210> SEQ ID NO 11
<211> LENGTH: 77
<212> TYPE: PRT
<213> ORGANISM: Acinetobacter calcoaceticus

<400> SEQUENCE: 11

Leu Asp His His Phe Arg His Ile Ala Leu Pro His Pro Gly Arg Ile
1               5                   10                  15

Arg Glu Leu Leu Ile Tyr Ile Ser Gln Glu His Ser Thr Leu Leu Asp
                20                  25                  30

Arg Ala Lys Pro Leu Trp Thr Cys Asn Ile Ile Glu Gly Ile Glu Gly
            35                  40                  45
```

-continued

```
Asn Arg Phe Ala Met Tyr Phe Lys Ile His His Ala Met Val Asp Gly
    50                  55                  60
Val Ala Gly Met Arg Leu Ile Glu Lys Ser Leu Ser His
65                  70                  75
```

HOST CELLS AND METHODS FOR PRODUCING ISOPRENYL ALKANOATES

CROSS-REFERENCES TO RELATED APPLICATIONS

This application claims benefit as a continuation application of PCT International Application No. PCT/US2008/68756, filed Jun. 30, 2008, which claims priority to U.S. provisional application No. 60/947,280, filed Jun. 29, 2007, the disclosures of which are incorporated by reference in their entireties.

STATEMENT AS TO RIGHTS TO INVENTIONS MADE UNDER FEDERALLY SPONSORED RESEARCH OR DEVELOPMENT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of production of isoprenyl alkanoate compounds, and in particular host cells that are genetically modified to produce isoprenyl alkanoate compounds.

BACKGROUND OF THE INVENTION

Petroleum derived fuels have been the primary source of energy for over a hundred years. Petroleum, however, has formed over millions of years in nature and is not a renewable source of energy. A significant amount of research in alternative fuels has been ongoing for decades. Within this field, ethanol has been studied intensively as a gasoline substitute and the use of ethanol as transportation fuel has been increasing recently (Gray et al., *Curr Opin Chem Biol* 2006, 10:141). However, the efficiency of ethanol as a fuel is still in debate (Pimentel, *Natural Resources Research* 2005, 14:65; Farrell et al., *Science* 2006, 311:506). There is interest to design several potential alternative fuel molecules other than ethanol, which can be produced biosynthetically, and to develop the biosynthetic pathways for enhanced production of the target fuel molecules using synthetic biology.

Currently, gasoline and diesel fuels are the two major transportation fuels. Gasoline is a complex mixture of hydrocarbons and additives for improving fuel performance. The carbon number of hydrocarbons in gasoline varies from 4 to 12, with branched alkanes, cyclic alkanes and aromatics being the most abundant. Diesel fuel is a mixture of many different hydrocarbons with the carbon numbers ranging from 9 to 23 with an average of 16. Usually n-alkanes and oxygenates in diesel fuel tend to increase the octane number, while branched or unsaturated hydrocarbons lower this value. Biodiesel has been of interest recently as a promising alternative fuel due to its renewability and environmental benefits. Biodiesel is a mixture of monoalkyl esters of long chain fatty acids derived from vegetable oils or animal fats. It is typically produced by acid or base-catalyzed transesterification of glycerin with methanol. The introduction of ester functionality in biodiesel improved the fuel properties, such as a higher octane number and an increased lubricating effect. Recently, enzymatic processes for fatty acid transesterification have been reported for the production of biodiesel (Kalscheuer et al., *Microbiol.* 2006, 152:2529-2536).

This present invention involves the biosynthesis of two hydrocarbons: isoprenoids and fatty acids. Isoprenoids are compounds derived from the five-carbon molecule, isopentenyl pyrophosphate. Investigators have identified over 29,000 individual isoprenoid compounds, with new ones continuously being discovered. Isoprenoids are often isolated from natural products, such as plants and microorganisms, which use isopentenyl pyrophosphate as a basic building block to form relatively complex structures. Vital to living organisms, isoprenoids serve to maintain cellular fluidity and electron transport, as well as function as natural pesticides, to name just a few of their roles in vivo. Furthermore, the pharmaceutical and chemical communities use isoprenoids as pharmaceuticals, nutriceuticals, flavoring agents, and agricultural pest control agents. Given their importance in biological systems and usefulness in a broad range of applications, isoprenoids have been the focus of much attention by scientists.

Conventional means for producing isoprenoids include extraction from biological materials (e.g., plants, microbes, and animals) and partial or total organic synthesis in the laboratory. Such means, however, have generally unsatisfactory as they involve the use of toxic solvents and provide a low yield of the desired isoprenoid. Recently, researchers have looked to the biosynthetic production of isoprenoids. U.S. Pat. No. 6,291,745 describes the production of limonene and other metabolites in plants. U.S. Pat. No. 6,190,895 describes nucleic acid sequences that code for the expression of 1-deoxyxylulose-5-phosphate synthase, an enzyme used in one biological pathway for the synthesis of isopentenyl pyrophosphate. U.S. Pat. No. 7,172,886 describes the cloning of genes for a mevalonate-isoprenoid pathway and synthesizing an isoprenoid or an isoprenoid precursor via the mevalonate pathway in a host cell. U.S. Pat. No. 7,183,089 describes a method for enhancing production of isoprenoid compounds in a host cell by modulating the level of hydroxymethylglutaryl-CoA (HMG-CoA) in the cell, such that the level of HMG-CoA is not toxic to the cell and does not substantially inhibit cell growth.

U.S. Pat. Nos. 5,460,949; 6,531,303; and 6,689,593; U.S. Pat. Pub. Nos. 2003/0148479; 2004/0029239; 2004/005678; 2004/0063182; 2004/0072323; 2004/0077039; 2004/0110259; and 2004/0194162; Martin et al. (2003) *Nat. Biotech.* 21(7):796-802; Polakowski et al. (1998) *Appl. Microbiol. Biotechnol.* 49: 67-71; Wilding et al. (2000) *J. Bacteriol.* 182(15): 4319-27; Donald et al. (1997) *Appl. Env. Microbiol.* 63:3341-3344; Jackson et al. (2003) *Organ. Lett.* 5:1629-1632; Hamano et al. (2001) *Biosci. Biotechnol. Biochem.* 65:1627-1635; Kuzuyama (2004) *Biosci. Biotechnol. Biochem.* 68(4): 931-934; Kazuhiko (2004) *Biotechnol. Lett.* 26: 1487-1491; Brock et al. (2004) *Eur. J. Biochem.* 271: 3227-3241; Choi, et al. (1999) *Appl. Environ. Microbiol.* 65: 4363-4368; Parke et al., (2004) *Appl. Environ. Microbiol.* 70: 2974-2983; Subrahmanyam et al. (1998) *J. Bacteriol.* 180: 4596-4602; Murli et al. (2003) *J. Ind. Microbiol. Biotechnol.* 30: 560-509. These references are hereby incorporated in their entireties by reference.

BRIEF SUMMARY OF THE INVENTION

The present invention provides for a method of producing an isoprenyl alkanoate in a genetically modified host cell. The method comprises culturing the genetically modified host cell under a suitable condition such that the culturing results in the genetically modified host cell producing an isoprenyl alkanoate. The host cell comprises an enzyme capable of catalyzing the esterification of an isoprenol and a straight-chain fatty acid.

The present invention also provides a method of producing a hydrogenated isoprenyl alkanoate by producing an isoprenyl alkanoate in a genetically modified host cell, recovering the isoprenyl alkanoate produced, and hydrogenating the recovered isoprenyl alkanoate to produce the hydrogenated isoprenyl alkanoate.

The present invention also provides for a genetically modified host cell useful for the methods of the present invention.

The present invention further provides for an isolated isoprenyl alkanoate or hydrogenated isoprenyl alkanoate produced from the method of the present invention.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
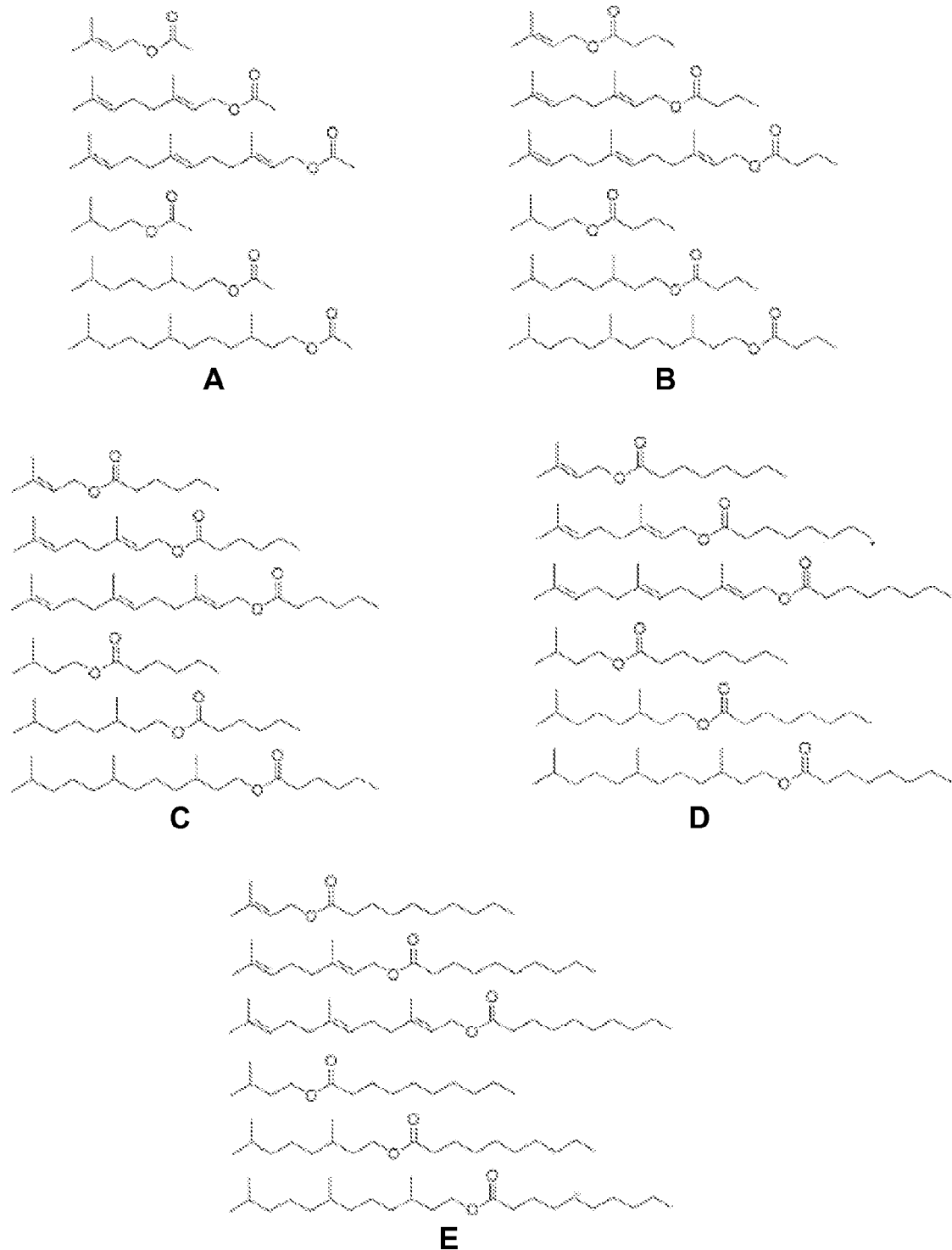
FIG. 1 shows the chemical structure of isoprenyl alkanoates. Panel A shows the chemical structure of the isoprenyl acetates (from top to bottom): isopentenyl acetate, geranyl acetate, farnesyl acetate, isopentyl acetate (isoamyl acetate), 3,7-dimethyloctyl acetate, and 3,7,11-trimethyldodecyl acetate. Panel B shows the chemical structure of the butyrate esters of (from top to bottom): isopentenol, geraniol, farnesol, isopentanol, 3,7-dimethyloctanol, and 3,7,11-trimethyldodecanol. Panel C shows the chemical structure of the hexanoate esters of (from top to bottom): isopentenol, geraniol, farnesol, isopentanol, 3,7-dimethyloctanol, and 3,7,11-trimethyldodecanol. Panel D shows the chemical structure of the octanoate esters of (from top to bottom): isopentenol, geraniol, farnesol, isopentanol, 3,7-dimethyloctanol, and 3,7,11-trimethyldodecanol. Panel E shows the chemical structure of the decanoate esters of (from top to bottom): isopentenol, geraniol, farnesol, isopentanol, 3,7-dimethyloctanol, and 3,7,11-trimethyldodecanol.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

In some embodiments of invention, for the method of producing one or more isoprenyl alkanoate in a host cell, the host cell produces one or more isoprenoid alcohol and the host cell comprises one or more enzymes that each possesses an alcohol acetyl acetyltransferase (AAT), wax ester synthase (WS/DGAT) or lipase activity capable of converting the isoprenoid alcohol into an isoprenoid alkanoate.

In some embodiments of invention, for the method for producing an isoprenyl alkanoate in a genetically modified host cell, the method comprises: culturing a genetically modified host cell under a suitable condition, wherein the genetically modified host cell comprises an enzyme capable of catalyzing the esterification of a isoprenol and a straight-chain fatty acid, such that the culturing results in the genetically modified host cell producing an isoprenyl alkanoate.

In some embodiments of invention, for the method for producing an isoprenyl alkanoate in a genetically modified host cell, the method comprises: culturing a genetically modified host cell under a suitable condition, wherein the genetically modified host cell comprises a nucleic acid construct encoding an enzyme capable of catalyzing the esterification of an isoprenol and a straight-chain fatty acid, and the culturing results in the expression of the enzyme, such that the culturing results in the genetically modified host cell producing an isoprenyl alkanoate.

In some embodiments of invention, for the method for producing an isoprenyl alkanoate in a genetically modified host cell, the method comprises: (a) introducing a nucleic acid construct encoding an enzyme capable of catalyzing the esterification of an isoprenol and a fatty acid into a genetically modified host cell; and (b) culturing the genetically modified host cell under a suitable condition such that the enzyme is expressed in the host cell; such that the culturing results in the genetically modified host cell producing an isoprenyl alkanoate.

In some embodiments of invention, the method further comprises the step of recovering the produced isoprenyl alkanoate, wherein the recovering step is concurrent or subsequent to the culturing step.

In some embodiments of invention, the method further comprise the step of hydrogenating the recovered isoprenyl alkanoate to produce a hydrogenated isoprenyl alkanoate, wherein the hydrogenating step is concurrent or subsequent to the recovering step; such that part or all of the recovered isoprenyl alkanoate is hydrogenated.

In some embodiments, the isoprenyl alkanoates are isoprenyl acetates (see FIG. 1, Panel A). The hydrogenation products of these isoprenyl acetates are also considered as fuel targets (see FIG. 1, Panel A). The use of isoamyl acetate as an emergency fuel or gasoline additive is disclosed in U.S. Pat. Nos. 5,853,433 and 6,353,143, which are incorporated in their entireties by reference.

In some embodiments, the host cells are capable of biosynthesis of the isoprenyl acetates (see FIG. 1, Panel A for some examples) by the coexpression of the appropriate terpene biosynthetic pathways and alcohol acetyltransferase (AAT) in *E. coli* or yeast. Terpene biosynthesis has been thoroughly studied for the production of many medicinally important isoprenoid natural products, and metabolic engineering of the biosynthetic pathway has also been intensively done to improve the production (Ro et al., *Nature* 2006, 440:940; Reiling et al., *Biotechnol. Bioeng.* 2004, 87:200; Martin et al., *Nat. Biotechnol.* 2003, 21:796, which are incorporated in their entireties by reference). Both mevalonate pathway and non-mevalonate pathway have been engineered to produce high titer of isopentenyl diphosphate (IPP), dimethylallyl diphosphate (DMAPP), geranyl diphosphate (GPP), and farnesyl diphosphate (FPP) (Martin et al., *Nat. Biotechnol.* 2003, 21:796). Instead of terpene cyclases which catalyze the formation of terpenes from diphosphate intermediates, pyrophosphases are expressed for the production of terpenol and they hydrolyze diphosphate intermediates to the corresponding primary alcohols (Song, *Appl. Biochem. Biotechnol.* 2006, 128:149, which is incorporated in its entirety by reference).

In some embodiments, the host cells are capable of biosynthesis of the esters of isoprenoid alcohols and fatty acids (see FIG. 1, Panels B-E for some examples). Such monoalkyl esters of long chain fatty acids, or mixtures thereof, are suitable as a biodiesel fuel. The fuel properties of biodiesel mainly come from the fatty acid portion of the molecule. Isoprenyls with straight-chains and lengths in the diesel fuel range (such as from sesquiterpenes to diterpenes) are better than branched isoprenyls with methyl branches and/or double bonds.

Enzymes capable of catalyzing the esterification of an isoprenol and a fatty acid, and constructs encoding thereof.

The enzymes capable of catalyzing the esterification of an isoprenol and a fatty acid include, but are not limited to, an alcohol acetyltransferase (AAT), wax ester synthase/diacylglycerol acyltransferase (WS/DGAT) or lipase, or a homologous enzyme thereof. A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

An AAT enzyme has an enzymatic activity for producing an acetate ester by transferring the acetyl group from acetyl-CoA to an alcohol. AAT is able to acetylate a broad range of alcohols. In certain embodiments, such alcohols have straight or branched chains having 1 to 6 carbon atoms. In particular, the AAT is derived from yeast, such as a *Saccharomyces* sp., such as *Saccharomyces cerevisiae* (or Baker's yeast) or *Saccharomyces pastorianus* (or Lager yeast or *Saccharomyces carlsbergensis*). A particular AAT suitable for use in this invention is *Saccharomyces cerevisiae* AAT which is described in U.S. Pat. Nos. 5,521,088 and 5,728,412, which are incorporated in their entireties by reference. The amino acid sequence and the nucleic acid sequence encoding thereof are disclosed in U.S. Pat. Nos. 5,521,088 and 5,728,412, which are incorporated in their entireties by reference. This AAT has been shown to have activity towards not only linear but also branched alcohol in *Clostridium acetobutylicum*, a suitable industrial strain for solvent production, and *E. coli* (Horton et al., *J. Ind. Microbiol. Biotechnol.* 2003, 30:427, which is incorporated in its entirety by reference). Table 1 lists the AAT enzymes suitable for use in the present invention (the references cited are hereby incorporated in their entireties by reference):

TABLE 1

| Genbank Accession No. | Enzyme | Organism | Percent identity with AAT1 of *Saccharomyces cerevisiae* | Reference |
| --- | --- | --- | --- | --- |
| P40353 | Alcohol O-acetyltransferase | *Saccharomyces cerevisiae* | 94% | Fujii et al., Appl. Environ. Microbiol. 60 (8): 2786-2792 (1994) |
| Q12677 | Alcohol acetyltransferase | *Saccharomyces pastorianus* | 94% | Fujii et al., Yeast 12(6): 593-598 (1996) |
| Q6XBT3 | Alcohol acetyltransferase I | *Saccharomyces pastorianus* | 94% | Verstrepen et al., Appl. Environ. Microbiol. 69(9): 5228-5237 (2003) |
| Q6XBT2 | Alcohol acetyltransferase I | *Saccharomyces cerevisiae* | 93% | Verstrepen et al., Appl. Environ. Microbiol. 69 (9): 5228-5237 (2003) |
| Q6XBS9 | Lager alcohol acetyltransferase I | *Saccharomyces pastorianus* | 76% | Verstrepen et al., Appl. Environ. Microbiol. 69 (9): 5228-5237 (2003) |
| Q12678 | Alcohol acetyltransferase | *Saccharomyces pastorianus* | 76% | Fujii et al., Yeast 12(6): 593-598 (1996) |

The references cited above in Table 1 are hereby incorporated in their entireties by reference.

A particular WS/DGAT suitable for use in this invention is *Acinetobacter calcoaceticus* WS/DGAT which, including its amino acid sequence and the nucleic acid sequence encoding thereof, is described in U.S. Pat. No. 7,118,896 and U.S. Pat. Pub. No. 2004/0009576, which are incorporated in their entireties by reference. Another suitable WS/DGAT is *Acinetobacter bayli* WS/DGAT, for example from strain ADP1, which is described by Vaneechoutte et al. (*Appl. Environ. Microbiol.* 2006, 72:932-936), which is incorporated in its entirety by reference. Further WS/DGAT proteins are identified in *Mycobacterium* and *Aradidopsis thaliana* and many species of *Acinetobacter* (Kalscheuer et al. *J. Biol. Chem.* 2003, 278:8075-8082). WS/DGAT is a very broad substrate range and includes short chain-length up to very long chain-length linear primary alkyl alcohols, cyclic, phenolic and secondary alkyl alcohols; diols and dithiols; mono- and diacylglycerols and sterols (Kalscheuer et al. *J. Biol. Chem.* 2003, 278:8075-8082; Kalscheuer et al. *Eur. J. Lipid Sci. Technol.* 2003, 105:578-584; Kalscheuer et al. *Appl. Environ. Microbiol.* 2004, 70:7119-7125; Stöveken et al. *J. Bacteriol.* 2005, 187:1369-1376; Uthoff et al. *Appl. Environ. Microbiol.* 2005, 71:932-936; Kalscheuer et al. *Microbiol.* 2006, 152: 2529-2536; which are incorporated in their entireties by reference). In some embodiments, the WS/DGAT is a prokaryotic WS/DGAT, such as mycobacteria WS/DGAT or an *Acinetobacter* WS/DGAT. The conserved amino acid residues and sequences are identified in FIG. 3 and in U.S. Pat. No. 7,118,896 (FIGS. 10 and 11), which is incorporated in its entirety by reference. Table 2 lists the WS/DGAT enzymes suitable for use in the present invention (the references cited are hereby incorporated in their entireties by reference):

TABLE 2

| Reference no. | Enzyme | Organism | Percent identity with WS/DGAT of *Acinetobacter* sp. strain ADP1 | Reference |
| --- | --- | --- | --- | --- |
| Q8GGG1 (Genbank Accession No.) | Wax ester synthase/acyl-CoA:diacylglycerol acyltransferase | *Acinetobacter* sp. ADP1 | 93% | Kalscheuer et al. J. Biol. Chem. 278(10): 8075-8082 (2003) |
| A3M8E4 (UniProt Accession No.) | Hypothetic protein | *Acinetobacter baumannii* strain ATCC 17978/NCDC KC 755 | 75% | Smith et al., Genes Dev. 21: 601-614 (2007) |

The references cited above in Table 2 are hereby incorporated in their entireties by reference.

Suitable lipases are described in Armstrong et al. (*Natural flavors produced by biotechnological processing*, American Chemical Society, Washington, D.C., 1989), which is incorporated in its entirety by reference.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521: 719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of acetyl-CoA, the starting material necessary for isoprenol or fatty acid production, is ensured. When added, the intermediate is present in an excess amount in the culture medium.

As the host cell grows and/or multiplies, expression of the enzymes necessary for producing the isoprenyl alkanoates is effected. Once expressed, the enzymes catalyze the steps necessary for carrying out the steps of isoprenol or fatty acid production and isoprenyl alkanoate production, i.e., converting acetyl-CoA into isoprenol and fatty acid. If an intermediate has been introduced, the expressed enzymes catalyze those steps necessary to convert the intermediate into the respective isoprenol and fatty acid. Any means for recovering the isoprenyl alkanoate from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC). Once the isoprenyl alkanoate is recovered, modification, such as hydrogenation, may be carried out in the laboratory on the isoprenyl alkanoate.

Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding an enzyme capable of catalyzing the esterification of an isoprenol and a fatty acid. Such enzymes include, but are not limited to, an alcohol acetyltransferase (AAT), wax ester synthase/diacylglycerol acyltransferase (WS/DGAT) or lipase, or a homologous enzyme thereof. The host cell also produces the isoprenol and the fatty acid either naturally and from the presence of further nucleic acid constructs that encode enzymes for synthesizing the isoprenol and/or fatty acid. The gene encoding the enzyme may be heterogous to the host cell or the gene may be native to the host cell but is operatively linked to a heterologous promoter and one or more control regions which result in a higher expression of the gene in the host cell. In other embodiments, the host cell does not naturally produce IPP and/or DMAPP, and comprises heterologous nucleic acid constructs capable of expressing one or more genes for producing IPP and/or DMAPP.

The enzyme capable of catalyzing the esterification of an isoprenol and a fatty acid can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

The host cells produce the isoprenol and the straight-chain fatty acid that participate in the esterification reaction that results in the isoprenyl alkanoate. The host cell comprises the genes encoding enzymes in the pathway from which the isoprenol is synthesized from acetyl-CoA. Similarly the host cell comprises the genes encoding enzymes in the pathway from which the fatty acid is synthesized from acetyl-CoA. These genes can either be native to the host cell or are heterologous to the host cell and introduced all or in part into the host cell either by integration into the host cell chromosome(s) or an expression vector, or both.

The host cells may comprises systems for synthesizing an isoprenyl pyrophosphate, e.g., "an isoprenyl pyrophosphate synthase", such as isopentenyl diphosphate (IPP), geranyl diphosphate (GPP), farnesyl diphosphate (FPP) and geranylgeranyl diphosphate (GGPP). Such systems are taught in U.S. Pat. Nos. 7,172,886 and 7,183,089, and U.S. Pat. Application Pub. No. 2003/0148479, 2006/0079476, 2007/0077616, 2007/0092931, and 2007/0099261, which are incorporated in their entireties by reference. Such methods include producing an isoprenoid or isoprenoid precursor in a genetically modified host cell, such as *E. coli*.

The host cells may express pyrophosphases which hydrolyze the isoprenyl diphosphate intermediates to the corresponding primary alcohols (Song, *Appl. Biochem. Biotechnol.* 2006, 128:149), including the isoprenyl alcohols. The host cells may be knocked out for or lack expression of any terpene cyclases which catalyze the formation of terpenes from diphosphate intermediates.

Figures 2, 3:
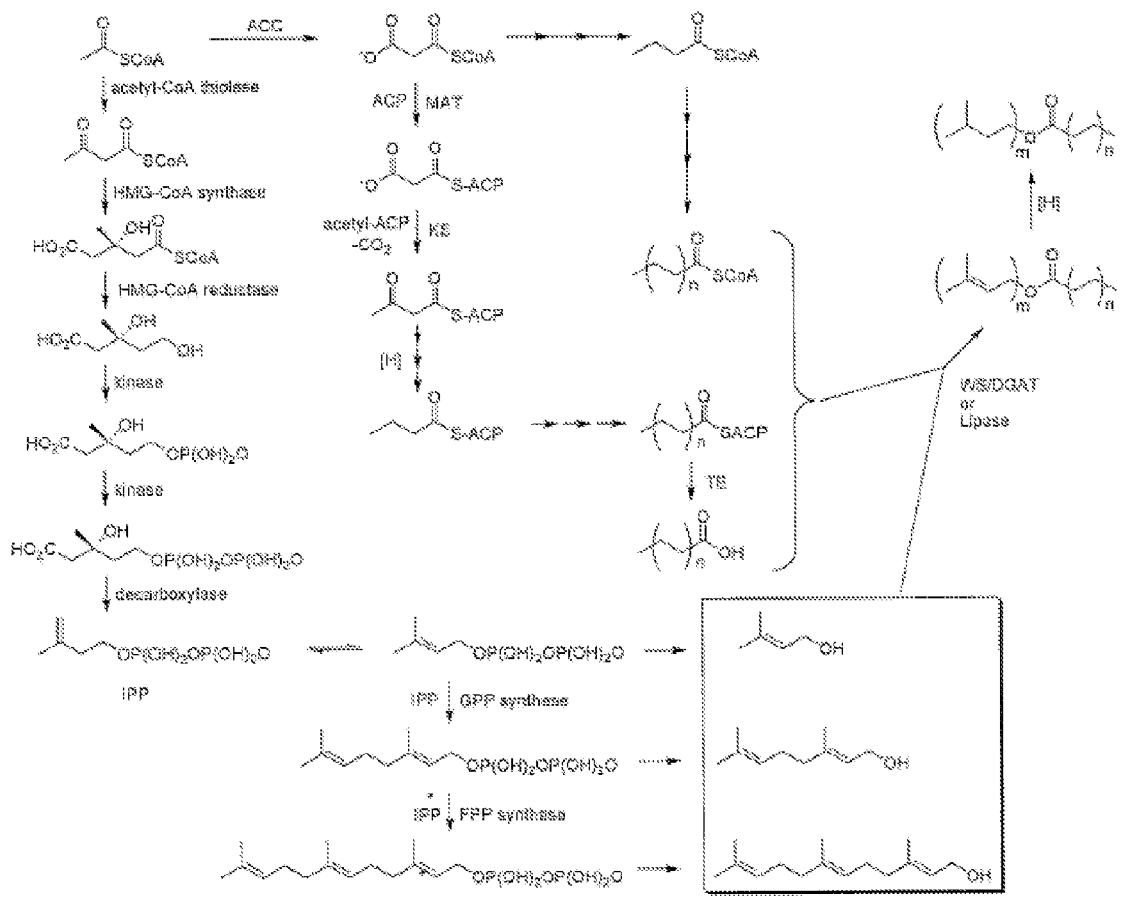
FIG. 2 shows the biosynthesis of isoprenyl alkanoates. Terpene biosynthetic pathway will generate isopentenol, geraniol, and farnesol. Various fatty acid synthetic pathways will generate a range of fatty acids with different but controllable length. Wax ester synthase-/acyl-coenzyme A: diacylglycerol acyltransferase (WS/DGAT) or lipases catalyze the esterification between terpenols and fatty acids, and the ester products are hydrogenated via chemical process.
FIG. 3 shows the amino acid sequence alignment of WS/DGAT from various organisms using the ClustalW program (Thompson et al., *Nucleic Acid Res.* 1994, 22:4673-4680, which is incorporated in its entirety by reference). The region corresponding to the *Acinetobacter calcoaceticus* ADP1 strain WS/DGAT amino acid residues 75-151 are shown. Conserved amino acid residues identical in 7 or more sequences are shaded in grey. The putative active site is boxed. *Mycobacterium tuberculosis* H37Rv: a, Rv3740c (SEQ ID NO:1); b, Rv3734c (SEQ ID NO:2); c, Rv1425 (SEQ ID NO:3); d, Rv3480c (SEQ ID NO:4); e, Rv2285 (SEQ ID NO:5); *Arabidopsis thaliana*: f, At5g53380 (SEQ ID NO:6); g, At5g16350 (SEQ ID NO:7); h, At5g12420 (SEQ ID NO:8); i, At5g22490 (SEQ ID NO:9); j, At1g72110 (SEQ ID NO:10); k, *A. calcoacetinus* ADP1 (SEQ ID NO:11). (Sequence alignment from Kalscheuer et al. *J. Biol. Chem.* 2003, 278:8075-8082, which is incorporated in its entirety by reference).

The enzymes that synthesize the isoprenol are shown FIG. 2 and are taught in U.S. Pat. Nos. 7,172,886; 7,183,089; and 7,192,751; and 2003/0148479, 2006/0079476, 2007/0077616, 2007/0092931, and 2007/0099261 (which are hereby incorporated by reference).

The enzymes that synthesize fatty acid are known in the art. In fatty acid biosynthesis, it is believed that acyl-ACP thioesterases (TE) have important roles in chain length control (Dehesh et al., *Plant Physiol.* 1996, 110:203, which is incorporated in its entirety by reference). Several TEs for specific production of medium chain length (C6 to C12) fatty acids are described (Naggert et al., *Biochem. J.* 1991, 273 (Pt 3): 787; Pollard et al., *Arch Biochem Biophys* 1991, 284:306; which are incorporated in their entireties by reference). A modular fatty acid biosynthetic pathway from *Trypanosoma brucei*, and different elongases that selectively produce C4, C10, C14 and C18 fatty acyl CoAs are described (Lee et al., *Cell* 2006, 126:691, which is incorporated in its entirety by reference). With modular polyketide synthases, the chain length can be easily controlled by the number of modules introduced (Floss et al., *Curr. Opin. Chem. Biol.* 1999, 3:592, which is incorporated in its entirety by reference). Short or medium chain length fatty acids can be biosynthesized by such various fatty acid synthases or modular polyketide synthases. In some embodiments, the level of acetyl-CoA carboxylase (ACC), which produces malonyl-CoA, an active building block of fatty acid biosynthesis, is increased (White et al., *Ann. Rev. Biochem.* 2005, 74:791, which is incorporated in its entirety by reference). Increased expression of ACC can be achieved by increasing the number of copies of the gene encoding ACC in the host cell in order to enhance or increase production of malonyl-CoA.

In some embodiments, the host cell may be genetically modified to produce heaxnoyl-CoA from hexanoic acid. For example, a host cell that produces hexanoic acid, e.g., a host cell that has been genetically modified to express a gene encoding hexanoate synthase (such as hexA and hexB genes from *Aspergillus* sp., e.g., *Bioorg Chem.* 2001 29:293-307, hereby incorporated by reference) can be further engineered to generate hexanoyl-CoA from the hexanoic acid. For example, in host cells in which hexanoic acid is not available as a free fatty acid, but is transferred to an acyl transferase (AT) that in turn transfers it to a polyketide synthase, hexanoic acid can be freed by hydrolyzing the covalent bond to the enzyme. Hexanoyl-CoA can be produced from the free hexanoic acid using a short chain acyl-CoA synthase. The covalent bond can be hydrozed, for example, using a thioesterase (TE) domain. For example, the TE domain from the 6-deoxy-erythronolide B (6 DEB) pathway has been shown to be promiscuous in hydrolyzing products from polyketide synthases. In some embodiments, an expression vector can be constructed in which a TE domain is fused to the AT enzyme. In other embodiments, TE may be fused to a truncated form of the PKS protein, downstream of the acyl carrier protein (ACP) domain. Such a construct closely mimics the enzymatic configurations that hydrolyze PKS products using this TE domain. The fusion protein comprising the TE domain can be expressed in a host cell that has been genetically modified to produce hexanoic acid, e.g., engineered to express an *Aspergillus* sp. hexA and hexB gene. In some embodiments, the gene encoding the fusion protein may be included in an expression vector that encodes a hexanoate synthase gene(s).

Isoprenoid alcohols (isopentanol, isopentenol, geraniol and farnesol) are generated in vivo via the hydrolysis of isoprenyl pyrophosphates as described above, such as via the mevalonate pathway.

Host cells that are suitable for expression of *Saccharomyces cerevisiae* AAT are *E. coli* and *Clostridium acetobutylicum*, which is described by Horton et al. (*J. Ind. Microbiol. Biotechnol.* 2003, 30, 427-432). Host cells that are suitable for expression of *Acinetobacter calcoaceticus* WS/DGAT is *E. coli*, which is described by Kalscheuer et al. (*Microbiol.* 2006, 152, 2529-2536).

A particular WS/DGAT suitable for use in this invention is *Acinetobacter calcoaceticus* WS/DGAT which is described in U.S. Pat. No. 7,118,896 and U.S. Pat. Pub. No. 2004/0009576, which are incorporated in their entireties by reference. Another suitable WS/DGAT is *Acinetobacter bayli* WS/DGAT, for example from strain ADP1, which is described by Vaneechoutte et al. (*Appl. Environ. Microbiol.* 2006, 72, 932-936; hereby incorporated by reference). WS/DGAT is a very broad substrate range and includes short chain-length up to very long chain-length linear primary alkyl alcohols, cyclic, phenolic and secondary alkyl alcohols; diols and dithiols; mono- and diacylglycerols and sterols (Kalscheuer et al. *J. Biol. Chem.* 2003, 278, 8075-8082; Kalscheuer et al. *Eur. J. Lipid Sci. Technol.* 2003, 105, 578-584; Kalscheuer et al. *Appl. Environ. Microbiol.* 2004, 70, 7119-7125; Stöveken et al. *J. Bacteriol.* 2005, 187, 1369-1376; Uthoff et al. *Appl. Environ. Microbiol.* 2005, 71, 932-936; Kalscheuer et al. *Microbiol.* 2006, 152, 2529-2536; which are hereby incorporated by reference).

Any prokaryotic or eukaryotic host cell may be used in the present method so long as it remains viable after being transformed with a sequence of nucleic acids. Generally, although not necessarily, the host microorganism is bacterial. In some embodiments, the bacteria is a cyanobacteria. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis*, and *Paracoccus* taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway.

Suitable eukaryotic cells include, but are not limited to, fungal, insect or mammalian cells. Suitable fungal cells are yeast cells, such as yeast cells of the *Saccharomyces* genus. In some embodiments the eukaryotic cell is an algae, e.g., *Chlamydomonas reinhardtii*, *Scenedesmus obliquus*, *Chlorella vulgaris* or *Dunaliella salina*.

The host cell can further be modified to comprise endogenous solvent efflux system such as AcrAB-TolC (Ramos et al., *Annu Rev Microbiol* 2002, 56:743; hereby incorporated by reference) to pump the isoprenyl alkanoates produced by the host cell out of the cell. When the host cell is capable of pumping the produced isoprenyl alkanoate out of the cell, the isoprenyl alkanoate can be recovered by removal of the supernatant in the host cell is being cultured.

Isoprenyl Alkanoate and Hydrogenated Forms Thereof

The isoprenyl alkanoate that can be produced using the present invention include isoprenyl acetate, isoprenyl butyrate, isoprenyl hexanoate, isoprenyl octanoate, and isoprenyl decanoate. The isoprenyl alkanoates are produced from the esterification of a suitable isoprenol and a fatty acid. Suitable isoprenols are isopentenol, isopentanol, geraniol, farnesol, geranylgeraniol, and the like. Suitable fatty acids are acetic acid (ethanoic acid), butyric acid (butanoic acid), hexanoic acid, octanoic acid, decanoic acid, and the like.

One skilled in the art can determine the various chain lengths of the subject isoprenyl alkanoates in order to change the fuel property of the isoprenyl alkanoates. The chain length of the molecules can be controlled for both the isoprenyl alcohols and fatty acids. Chain length control of the isoprenoids is achieved by introducing different terpene synthases as described in U.S. Pat. Nos. 7,172,886; 7,183,089; and 7,192,751; and 2003/0148479, 2006/0079476, 2007/0077616, 2007/0092931, and 2007/0099261, which are incorporated in their entireties by reference.

In some embodiments, the isoprenyl alkanoate has the ester linkage in or near the middle of the molecule. This confers advantages such as increased lubrication and more complete combustion. When the isoprenyl alkanoate is involved in a combustion process, the ester linkage is likely to break and form two gasoline-like molecules. In the event that the ester linkage does not break, the bond may easily rotate and help internal involvement of radical formation as observed in normal diesel fuel combustion.

To produce isoprenyl alkanoates with desired fuel properties, the chain lengths of the molecules can to be controlled for both the isoprenyl alcohols and the fatty acids. Chain length control of the isoprenoids is achieved by introducing different terpene synthases and/or different fatty acid synthases, as described herein. Short or medium chain length fatty acids can be biosynthesized by various fatty acid synthases or modular polyketide synthases. In either case, the overexpression of acetyl-CoA carboxylase (ACC), which produces malonyl-CoA, an active building block of fatty acid biosynthesis (White et al., *Annu. Rev. Biochem.* 2005, 74:791, which is incorporated in its entirety by reference) can be engineered by increasing the number of copies of this gene into the host cell for enhanced production of malonyl-CoA (FIG. 2).

Some examples of isoprenyl alkanoate produced using the present invention are disclosed in FIG. 1. Further examples include geranylgeranyl alkanoates, and hydrogenated geranylgeranyl alkanoates.

The recovered or isolated isoprenyl alkanoate can be hydrogenated using any suitable means known to one skilled in the art. One suitable means is through the use of an effective catalyst for the hydrogenation of alkenes, such as tris(triphenylphosphine)carbonylrhodium hydride ($(Ph_3P)_3RhHCO$).

The present invention provides for an isolated isoprenyl alkanoate or hydrogenated isoprenyl alkanoate produced from the method of the present invention. Isolating the isoprenyl alkanoate involves the separating at least part or all of the host cells, and parts thereof, from which the isoprenyl alkanoate was produced, from the isoprenyl alkanoate. The isolated isoprenyl alkanoate may be free or essentially free of impurities formed from at least part or all of the host cells, and parts thereof. The isolated isoprenyl alkanoate is essentially free of these impurities when the amount and properties of the impurities do not interfere in the use of the isoprenyl alkanoate as a fuel, such as a fuel in a combustion reaction. These host cells are specifically cells that do not in nature produce the isoprenyl alkanoate. The impurities are no more than 5%, 1%, 0.5%, 0.1%, 0.05%, or 0.01% by weight of a composition comprising one or more of the isoprenyl alkanoates, or the hydrogenated forms thereof.

The present invention also provides for a combustible composition comprising an isolated isoprenyl alkanoate or hydrogenated isoprenyl alkanoate and cellular components, wherein the cellular components do not substantially interfere in the combustion of the composition. The cellular components include whole cells or parts thereof. The cellular components are derived from host cells which produced the isoprenyl alkanoate or the isoprenyl alkanoate from which the hydrogenated isoprenyl alkanoate was derived.

The isoprenyl alkanoates, or hydrogenated isoprenyl alkanoates, of the present invention are useful as fuels as chemical source of energy that can be used as an alternative to petroleum derived fuels, ethanol and the like. For example, in some embodiments, isoprenyl alkanoates that have a cetane number that is comparable to or higher than the cetane number of commercial #2 diesel (cetane number of about 42) are produced as described herein. In some embodiments, geranyl hexnoate, 3,7-dimethyloctyl hexanoate; geranyl octanoate, or 3,7-di-methyloctyl octanoate can be used as an alternative to petroleum-derived fuels.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Production of Isoprenyl Acetates in a Host Cell

The pMevT plasmid (containing the genes for synthesizing mevalonate from acetyl-CoA) and pMBI (containing the genes for synthesizing IPP and DMAPP from mevalonate) are introduced into *E. coli* DH1, which then is capable of expressing IPP and DMAPP. The method for constructing the pMevT plasmid, and nucleotide sequence, are taught in U.S. Pat. No. 7,183,089, which is incorporated in its entirety by reference. The method for constructing the pMBI plasmid is taught in Martin et al. (*Nature Biotechnol.* 21:796-802 (2003)), which is incorporated in its entirety by reference.

To prepare an *E. coli* host cell capable of geraniol synthesis, a plasmid capable of stable maintenance in *E. coli* and expression of the *Abies grandis* geranyl diphosphate synthase (AgGPPS2; the amino acid and nucleotide sequences of AgGPPS2 are taught in U.S. Application Pub. No. 2005/0204417, which is incorporated in its entirety by reference) or S81F-GPP mutant of *Haematococcus pluvialis* IspA (taught in Reiling et al., *Biotechnol. Bioeng.* 87(2):200-212, 2004, which is incorporated in its entirety by reference), and *Ocimum basilicum* (sweet basil) geraniol synthase (GES), which is disclosed by Ijima et al. (*Plant Physiology* 134:370-379 (2004), which is incorporated in its entirety by reference).

To prepare an *E. coli* host cell capable of farnesol synthesis, first a plasmid is constructed containing the mevalonate pathway genes of pMevT and pMBIS. The pMBIS plasmid contains the ispA gene (encoding FPP synthase). The pMBIS plasmid, including its nucleotide sequence, is taught in U.S. Pat. No. 7,183,089, which is incorporated in its entirety by reference. This resultant plasmid is then introduced into *E. coli* DH1.

Primers can be designed to PCR *Saccharomyces cerevisiae* AAT from *S. cerevisiae* genomic DNA and cloned into a suitable *E. coli* expression vector. The resultant plasmid is introduced into an *E. coli* host cell also containing the pMevT and pMBI plasmids. The resulting transformant is cultured in a suitable medium, such as Luria broth (LB) medium at 37° C. with the appropriate antibiotics to maintain the plasmids. The enzymes are induced using the appropriate inducers, such as IPTG or propionate, and incubated at 30° C. for 3-7 days. The induction of the enzymes results in the production of isopentenyl acetate.

If the host cell also contains the plasmid expressing AgGPPS2 or the S81F-GPP mutant of *H. pluvialis* IspA, then culturing the host cell in the suitable medium results in the production of geranyl acetate If the host cell also contains the plasmid containing the mevalonate pathway genes of pMevT and pMBIS, then culturing the host cell in the suitable medium results in the production of farnesyl acetate.

The isopentenyl acetate and farnesyl acetate can be purified and analyzed using a gas chromatography-mass spectrometer (GC-MS). The purified isopentenyl acetate, geranyl acetate, and farnesyl acetate can each then be hydrogenated using $(Ph_3P)_3RhHCO$ to produce isopentyl acetate (isoamyl acetate), 3,7-dimethyloctyl acetate, and 3,7,11-trimethyldodecyl acetate, respectively.

An exemplary expression construct that has been employed for geranyl acetate production is pET29-AgGPPS2-GES-AAT1, where AgGPPS2, to produce GPP, is from *Abies grandis*; GES, to produce gerianol, is from sweet basil; and AAT1, to produce geranyl acetate, is from *Saccharomyces cerevisiae*. The vector was used in a two-plasmid system in *E. coli* DH1 strain along with pMBI. The pET29-AgGPPS2-GES-AAT1 was introduced into an *E. coli* host cell containing pMBI. The resulting transformants were cultured in TB medium at 37° C. with the appropriate antibiotics to maintain the plasmids. The enzymes were induced using 200 µM IPTG, supplemented with 10 mM mevalonate after induction, overlaid with 10% dodecane, and incubated at 30° C. After 48 hours of incubation, 100 µL of the deodecane layer was diluted with 900 µL of ethyl acetate (5 µg/mL caryophellen was used as an internal standard). GC/MS analysis confirmed the production of geranyl acetate (50 mg/L).

Yeast

Constructs encoding *Saccharomyces cervisiae* AAT and GPP synthase are also evaluated in yeast. In exemplary embodiments, constructs are based on a 3-promoter version of pESC-Leu2d, for expression in *Saccharomyces cerevisiae* strain EPY300. The following are examples of such constructs:

TABLE 3

| Contruct | GPP synthase | Geraniol Synthase | Acetylase | Major Product* |
|---|---|---|---|---|
| pCF306 | AgGPPS2 | | | 1 |
| pCF307 | AgGPPS2 | GES | | 2 |
| pCF308 | AgGPPS2 | GES | AAT1 | 3 |
| pCF315 | AgGPPS2 | | AAT1 | 3 |
| pCF309 | AgGPPS2t | | | 1 |
| pCF310 | AgGPPS2t | GES | | 2 |
| pCF311 | AgGPPS2t | GES | AAT1 | 3 |
| pCF316 | AgGPPS2t | | AAT1 | 3 |
| pCF312 | ERG20 K197E | | | 1 |
| | ERG20 | | | 2 |
| pCF313 | K197E | GES | | |
| | ERG20 | | | 3 |
| pCF314 | K197E | GES | AAT1 | |
| | ERG20 | | | 3 |
| pCF317 | K197E | | AAT1 | |
| pCF318 | ERG20 | | | 4 |
| pCF319 | ERG20 | GES | | 5 |
| pCF320 | ERG20 | GES | AAT1 | 6 |
| pCF321 | ERG20 | | AAT1 | 6 |
| pCF322 | ERG20 | NudF | | 5 |
| pCF323 | ERG20 | NudF | AAT1 | 6 |

Figures 4, 5:
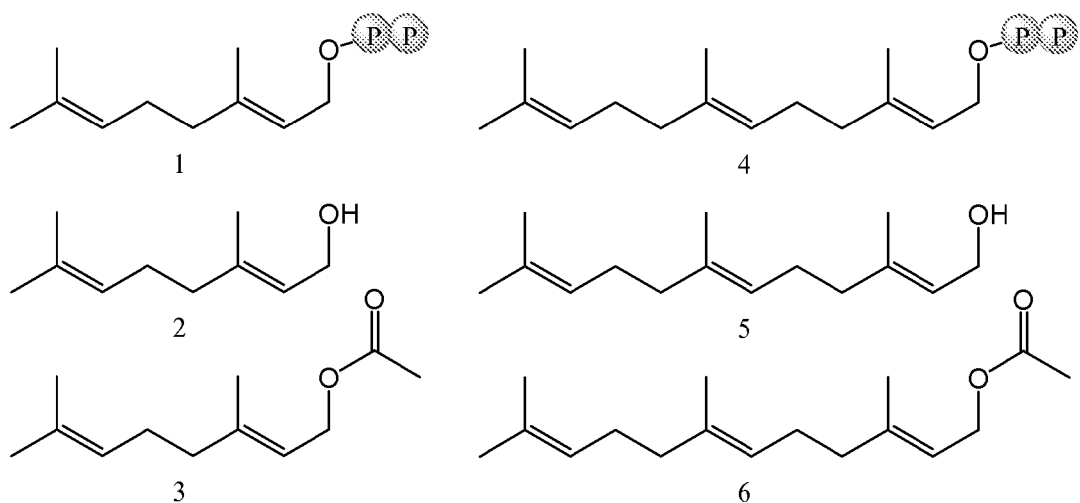
FIG. 4 depicts the products corresponding to the "Major Product" number in Table 3.
FIG. 5 depicts preliminary combustion data. Panel A shows the combustion data. Panel B shows the chemical structure of each molecule.
Figure 5:
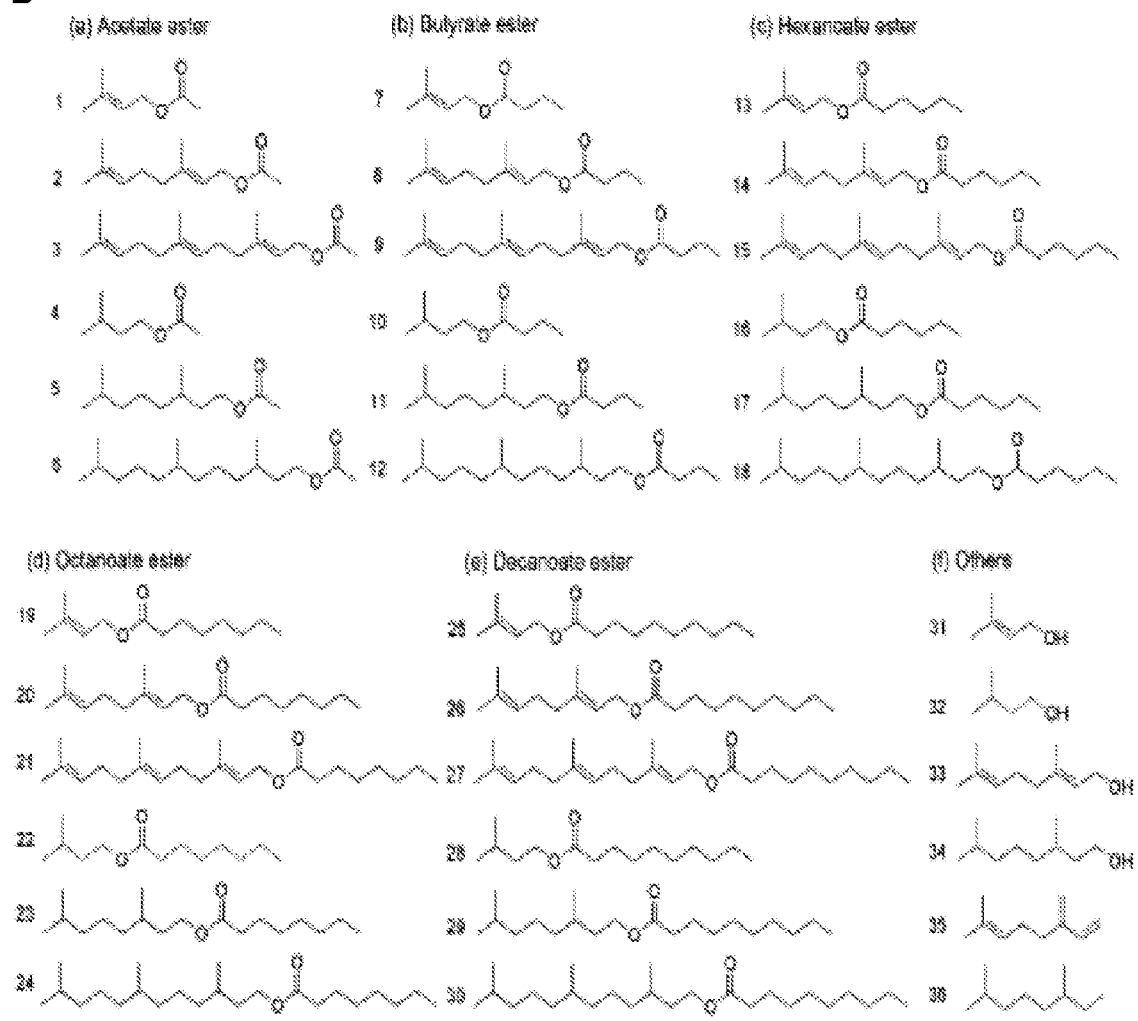

AgGPPS2 = GPP synthase from *Abies grandis*
AgGPPS2t = GPP synthase from *Abies grandis*, truncated to remove plastid signaling sequence
ERG20 = FPP synthase from *Saccharomyces cerevisiae*
ERG20 K197E = Previously characterized mutant shown to produce GPP:FPP at 2:1
EPY300 = *S. cerevisiae* strain capable of producing high levels of isoprenoids
*The products corresponding to the numbers 1-6 are shown in FIG. 4.

EXAMPLE 2

Production of Isoprenyl Alkanoates in a Host Cell

A plasmid capable of maintenance in *E. coli* is used to construct a plasmid capable of expressing a fatty acid synthase (FAS), such as hexanoate synthase (such as hexA and hexB of *Aspergillus* sp.), or elongases (such as, ELO1 (AAX70671), ELO2 (AAX70672), and ELO3 (AAX70673) from *Trypanosoma*), or FabA and FabB from *E. coli*. Further, the same plasmid, or another plasmid plasmid capable of maintaince in *E. coli*, is constructed to express thioesterase (TE) and acyl-CoA synthase (ACS). The TE hydrolyzes enzyme-bound fatty acid to free fatty acid, while the ACS converts the free fatty acid to fatty acid acyl-CoA.

Primers can be designed to PCR *Acinetobacter calcoaceticus* WS/DGAT from *A. calcoaceticus* genomic DNA and cloned into a suitable *E. coli* expression vector. The resultant plasmid is introduced into an *E. coli* host cell also containing the pMevT and pMBI plasmids. The resulting transformant is cultured in a suitable medium, such as Luria broth (LB) medium at 37° C. with the appropriate antibiotics to maintain the plasmids. The enzymes are induced using the appropriate inducers, such as IPTG or propionate, and incubated at 30° C. for 3-7 days. The induction of the enzymes results in the production of isopentenyl acetate.

To prepare an *E. coli* host cell capable of geraniol synthesis, a plasmid capable of stable maintenance in *E. coli* and expression of the *Abies grandis* geranyl diphosphate synthase (AgGPPS2; the amino acid and nucleotide sequence of AgGPPS2 are taught in U.S. Application Pub. No. 2005/0204417) or S81F-GPP mutant of *Haematococcus pluvialis* IspA (taught in Reiling et al., *Biotechnol. Bioeng.* 87(2):200-212, 2004; hereby incorporated by reference), and *Ocimum basilicum* (sweet basil) geraniol synthase (GES), which is disclosed by Ijima et al. (*Plant Physiology* 134:370-379 (2004); hereby incorporated by reference). To prepare an *E. coli* host cell capable of farnesol synthesis, the pAM45 plasmid is introduced into *E. coli* DH1.

Primers can be designed to PCR *Saccharomyces cerevisiae* AAT from *S. cerevisiae* genomic DNA and cloned into a suitable *E. coli* expression vector. The resultant plasmid is introduced into an *E. coli* host cell also containing the pMevT and pMBI plasmids, and the plasmids with the fatty acid biosynthetic gene(s). The resulting transformant is cultured in a suitable medium, such as Luria broth (LB) medium at 37° C. with the appropriate antibiotics to maintain the plasmids. The enzymes are induced using the appropriate inducers, such as IPTG or propionate, and incubated at 30° C. for 3-7 days. The induction of the enzymes results in the production of isopentenyl alkanoate.

If the host cell also contains the plasmid expressing AgG-PPS2 or the S81F-GPP mutant of *H. pluvialis* IspA, then culturing the host cell in the suitable medium results in the production of geranyl alkanoate.

If the host cell also contains the plasmid containing the mevalonate pathway genes of pMevT and pMBI, then culturing the host cell in the suitable medium results in the production of farnesyl alkanoate.

An exemplary three-plasmid system to produce geranyl hexanoate from glucose employs the pMevT plasmid genes and pMBI plasmid genes on one plasmid to produce IPP/DMAPP. A second plasmid is pLA9-GPPS-GES-WS/DGAT and the third plasmid is pTrc99-HexA-HexB-TE-[Acyl-CoA synthase], using hexA and hexB nucleic acids from *Aspergillus*. The three plasmids are introduced into *E. coli* DH1 cells for the production of geranyl hexanoate.

The isopentenyl alkanoate, geranyl alkanoate, and farnesyl alkanoate can be purified and analyzed using a gas chromatography-mass spectrometer (GC-MS). The purified isopentenyl alkanoate, geranyl alkanoate, and farnesyl alkanoate can each then be hydrogenated using $(Ph_3P)_3RhHCO$ to produce isopentyl alkanoate, 3,7-dimethyloctyl alkanoate, and 3,7,11-trimethyldodecyl alkanoate, respectively.

EXAMPLE 3

Fuel Property Test

A schematic of the synthesis of potential fuel molecules: esterification of isoprenyl alcohol and short chain fatty acyl chloride is shown below.

Fuel property testing of potential fuel molecules was conducted using IQT (ignition quality tester) to obtain a preliminary cetane number. Cetane number prediction is based on the fuel structure and the preliminary combustion data. This analysis (FIG. 5) identified geranyl hexanoate, 3,7-dimethyloctyl hexanoate, geranyl octanoate, and 3,7-dimethyloctyl octanoate as having comparable or higher cetane numbers in comparison to commercial #2 diesel (Cetane number ~42).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing an isoprenyl alkanoate in a genetically modified host cell, the method comprising:
    (a) culturing a genetically modified host cell, wherein the genetically modified host cell comprises (i) an enzyme capable of catalyzing the esterification of a isoprenol and a straight-chain fatty acid, and (ii) one or more nucleic acid constructs encoding an isoprenyl pyrophosphate synthase and a pyrophosphase that is capable of hydrolyzing an isoprenyl diphosphate to an alcohol,
    such that the culturing results in the genetically modified host cell producing an isoprenyl alkanoate; wherein the isoprenyl alkanoate is one selected from the group consisting of isoprenyl acetate, isoprenyl butyrate, isoprenyl hexanoate, isoprenyl octanoate, and isoprenyl decanoate.

2. The method of claim 1, wherein the genetically modified host cell comprises a nucleic acid construct encoding the enzyme capable of catalyzing the esterification of an isoprenol and a fatty acid, and the culturing results in the expression of the enzyme.

3. The method of claim 1, wherein the host cell comprises a single nucleic acid construct that encodes the the enzyme capable of catalyzing the esterification of the isoprenol and the straight-chain fatty acid, the isoprenyl pyrophosphate synthase and the pyrophosphase.

4. The method of claim 2, further comprising the step of: introducing the nucleic acid construct into the genetically modified host cell, wherein the introducing step is prior the culturing step.

5. The method of claim 1, further comprising the step of:
    (b) recovering the produced isoprenyl alkanoate, wherein the recovering step is concurrent or subsequent to the culturing step.

6. The method of claim 5, further comprising the step of:
    (c) hydrogenating the recovered isoprenyl alkanoate to produce a hydrogenated isoprenyl alkanoate, wherein the hydrogenating step is concurrent or subsequent to the recovering step;
    such that part or all of the recovered isoprenyl alkanoate is hydrogenated.

7. The method of claim 1, wherein the enzyme is an alcohol acetyltransferase (AAT), wax ester synthase (WS/DGAT) or lipase, or a homologous enzyme thereof.

8. The method of claim 1, wherein the AAT is *Saccharomyces cerevisiae* AAT.

9. The method of claim 1, wherein the WS/DGAT is *Acinetobacter calcoaceticus* WS/DGAT.

10. The method of claim 1, wherein the isoprenyl acetate is isopentenyl acetate, geranyl acetate, or farnesyl acetate.

11. The method of claim 1, wherein the isoprenyl butyrate is isopentenyl butyrate, geranyl butyrate, or farnesyl butyrate.

12. The method of claim 1, wherein the isoprenyl hexanoate is isopentenyl hexanoate, geranyl hexanoate, or farnesyl hexanoate.

13. The method of claim 1, wherein the isoprenyl octanoate is isopentenyl octanoate, geranyl octanoate, or farnesyl octanoate.

14. The method of claim 1, wherein the isoprenyl decanoate is isopentenyl decanoate, geranyl decanoate, or farnesyl decanoate.

15. The method of claim 6, wherein the hydrogenated isoprenyl alkanoate is one selected from the group consisting of isoprenyl acetate, isoprenyl butyrate, isoprenyl hexanoate, isoprenyl octanoate, and isoprenyl decanoate.

16. The method of claim 15, wherein the isoprenyl acetate is isopentyl acetate, 3,7-dimethyloctyl acetate, or 3,7,11-trimethyldodecyl acetate.

17. The method of claim 15, wherein the isoprenyl butyrate is isopentanyl butyrate, 3,7-dimethyloctanyl butyrate, or 3,7,11-trimethyldodecanyl butyrate.

18. The method of claim 15, wherein the isoprenyl hexanoate esters is isopentanyl hexanoate, 3,7-dimethyloctanyl hexanoate, or 3,7,11-trimethyldodecanyl hexanoate.

19. The method of claim 15, wherein the isoprenyl octanoate is isopentanyl octanoate, 3,7-dimethyloctanyl octanoate, or 3,7,11-trimethyldodecanyl octanoate.

20. The method of claim 15, wherein the isoprenyl decanoate is isopentanol decanoate, 3,7-dimethyloctanyl decanoate, or 3,7,11-trimethyldodecanyl decanoate.

21. The method of claim 1, wherein the host cell is a eubacteria.

22. The method of claim 21, wherein the host cell is one selected from the *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis*, and *Paracoccus* taxonomical classes.

23. The method of claim 22, wherein the host cell is *Escherichia coli*.

24. The method of claim 1, wherein the host cell is an algal, fungal, insect or mammalian cell line.

25. The method of claim 24, wherein the host cell is a yeast.

26. A genetically modified host cell comprising: (i) a nucleic acid construct encoding an enzyme capable of catalyzing the esterification of an isoprenol and a straight-chain fatty acid into an isoprenyl alkanoate, and (ii) one or more nucleic acid constructs encoding an isoprenyl pyrophosphate synthase and a pyrophosphase that is capable of hydrolyzing an isoprenyl diphosphate to an alcohol; wherein the isoprenyl alkanoate is one selected from the group consisting of isoprenyl acetate, isoprenyl butyrate, isoprenyl hexanoate, isoprenyl octanoate, and isoprenyl decanoate.

27. The host cell of claim 26, wherein host cell prior to genetic modification does not produce the isoprenyl alkanoate.

* * * * *